United States Patent [19]

Rathjen et al.

[11] Patent Number: 5,587,457
[45] Date of Patent: Dec. 24, 1996

[54] NEUTROPHIL STIMULATING PEPTIDES

[75] Inventors: Deborah A. Rathjen, Thornleigh; Antonio Ferrante, Mount Osmond, both of Australia

[73] Assignee: Peptide Technology Limited, Australia

[21] Appl. No.: 107,235

[22] Filed: Aug. 16, 1993

Related U.S. Application Data

[63] Continuation-in-part of Ser. No. 930,415, filed as PCT/AU91/00086, Mar. 12, 1991, abandoned.

[30] Foreign Application Priority Data

Mar. 12, 1990 [AU] Australia ................................. PJ9065

[51] Int. Cl.⁶ .......................... A61K 38/00; A61K 37/02; C07K 7/06; C07K 14/00
[52] U.S. Cl. ............................................. 530/326; 530/327
[58] Field of Search .................................. 530/326, 328, 530/327; 514/16, 15

[56] References Cited

U.S. PATENT DOCUMENTS 4,650,674  3/1987  Aggarwal et al. ........................ 424/85

FOREIGN PATENT DOCUMENTS

| 2005061 | 6/1990 | Canada . | |
|---|---|---|---|
| 2005060 | 6/1990 | Canada . | |
| AU9000337 | 2/1991 | WIPO . | |
| 9102078 | 2/1991 | WIPO | A61K 37/02 |
| 9113908 | 9/1991 | WIPO | A61K 37/02 |
| 9114702 | 10/1991 | WIPO | A61K 37/02 |
| 9117180 | 11/1991 | WIPO | A61K 37/02 |
| 9203145 | 3/1992 | WIPO | A61K 37/02 |
| 9301211 | 1/1993 | WIPO | A61K 37/02 |

OTHER PUBLICATIONS

Socher, et al, Proc. Natl. Acad of Sci. USA, vol. 84, pp. 8829–8833, 1987.
Rathjen et al, Immunology, 80, 293–299, 1993.
Shalaby, et. al., 1985, J. Immunol. 135: 2069–2073 Activation of Human Polymorphonuclear Neutrophil Functions by Interferon gamma and Tumor Necrosis Factor.
Djeu, et. al., 1986, J. Immunol. 137: 2980–2984 Growth Inhibition of *Candida albicans* by Human Polymorphonuclear Neutrophils: Activation by Interferon gamma and Tumor Necrosis Factor.
Klebanoff, et. al., 1986, J. Immunol. 136: 4220–4225 Stimulation of Neutrophils by Tumor Necrosis Factor.
Tsujimoto, et. al., 1986, Biochem. Biophys. Res. Comm. 137: 1094–1100 Tumor Necrosis Factor Provokes Superoxide Anion Generation from Neutrophils.
Graybill, 1988, J. Inf. Dis. 158: 623–626 Histoplasmosis and AIDS.
Murphy, et. al., 1988, J. Inf. Dis. 158: 627–630 Impairment of Neutrophil Bactericidal Capacity in Patients with AIDS.
Cybulsky, et. al., 1988, J. Immunol. 140: 3144–3149 Neutrophil Leukocyte Emigration Induced by Endotoxin: Mediator Roles of Interleukin 1 and tumor Necrosis Factor alpha.
Fermate, et. al., 1988, Int. Archs. Allergy Appl. Immunol. 86: 82–91 Effects of Tumour Necrosis Factor Alpha on Interleukin–1 Alpha and Beta on Human Neutrophil Migration, Respiratory Burst and Degranulation.
Shau, 1988, J. Immunol. 144: 234–240 Characteristics and Mechanism of Neutrophil–Mediated Cytostasis Induced by Tumor Necrosis Factor.
Ferrante, 1989, J. Inf. Imm. 57: 2115–2122 Tumor Necrosis Factor Alpha Potentiates Neutrophil Antimicrobial Activity: Increased Fungicidal Activity against *Torulopis glabrata* and *Candida albicans* and Associated Increased in Oxygen Radical Production.
Kumaratilake, et. al., 1991, J. Immunol. 146: 762–767 The Role of T Lymphocytes in Immunity to *Plasmodium falciparum*.
Socher, Susan H. et al., P.N.A.S. (USA) 84: 8829–8833 (1987).

*Primary Examiner*—Elizabeth C. Weimar
*Assistant Examiner*—S. G. Marshall
*Attorney, Agent, or Firm*—Banner & Allegretti, Ltd.

[57] ABSTRACT

The present invention provides peptides capable of stimulating neutrophils. In particular, the peptides prime neutrophils for a respiratory burst following treatment with N-formyl-L-methionyl-L-leucyl-Lphenylalanine. The peptides have an amino acid sequence substantially corresponding to amino acids 54 to 94 of FIG. 1 or a part thereof. These peptides may also be used in the treatment of a subject having depressed neutrophil function.

6 Claims, 8 Drawing Sheets

VRSSSRTPSD$^{10}$KPVAHVVANP$^{20}$QAEGQLQWLN$^{30}$RRANALLANG$^{40}$

VELRDNQLVV$^{50}$PSEGLYLIYS$^{60}$QVLFKGQGCP$^{70}$STHVLLTHTI$^{80}$

SRIAVSYQTK$^{90}$VNLLSAIKSP$^{100}$CQRETPEGAE$^{110}$AKPWYEPIYL$^{120}$

GGVFQLEKGD$^{130}$RLSAEINRPD$^{140}$YLDFAESGQV$^{150}$YFGIIAL$^{157}$

FIG. 1

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 157 amino acids
        ( B ) TYPE: amino acid
        ( D ) TOPOLOGY: linear (ii) MOLECULE TYPE: protein (ix) FEATURE:
  (A) NAME/KEY: Peptide
  (B) LOCATION: 1..157
  (D) OTHER INFORMATION: /note= "HUMAN TNF)"

(xi) SEQUENCE DESCRIPTION: SEQ ID NO:1:

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
 65                 70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
               100                 105                 110

Pro Trp Tyr Glu Pro Ile Tyr Leu Gly Gly Val Phe Gln Leu Glu Lys
           115                 120                 125

Gly Asp Arg Leu Ser Ala Glu Ile Asn Arg Pro Asp Tyr Leu Asp Phe
       130                 135                 140

Ala Glu Ser Gly Gln Val Tyr Phe Gly Ile Ile Ala Leu
145                 150                 155
```

(2) INFORMATION FOR SEQ ID NO:2:

(i) SEQUENCE CHARACTERISTICS:
    (A) LENGTH: 10 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..10
    (D) OTHER INFORMATION: /note= "PEPTIDE 275 (111-120)"

(xi) SEQUENCE DESCRIPTION: SEQ ID NO:2:

```
Ala Lys Pro Trp Tyr Glu Pro Ile Tyr Leu
 1               5                  10
```

(2) INFORMATION FOR SEQ ID NO:3:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..18
    (D) OTHER INFORMATION: /note= "PEPTIDE 301 (1-18)"

(xi) SEQUENCE DESCRIPTION: SEQ ID NO:3:

```
Val Arg Ser Ser Ser Arg Thr Pro Ser Asp Lys Pro Val Ala His Val
 1               5                  10                  15
```

Val Ala (2) INFORMATION FOR SEQ ID NO:4:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "PEPTIDE 302 (43-58)"

(xi) SEQUENCE DESCRIPTION: SEQ ID NO:4:

```
Leu  Arg  Asp  Asn  Gln  Leu  Val  Val  Pro  Ser  Glu  Gly  Leu  Tyr  Leu  Ile
1                   5                        10                       15
```

(2) INFORMATION FOR SEQ ID NO:5:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "PEPTIDE 303 (94-109)"

(xi) SEQUENCE DESCRIPTION: SEQ ID NO:5:

```
Leu  Ser  Ala  Ile  Lys  Ser  Pro  Cys  Gln  Arg  Glu  Thr  Pro  Glu  Gly  Ala
1                   5                        10                       15
```

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..21
        (D) OTHER INFORMATION: /note= "PEPTIDE 304 (63-83)"

(xi) SEQUENCE DESCRIPTION: SEQ ID NO:6:

```
Leu  Phe  Lys  Gly  Gln  Gly  Cys  Pro  Ser  Thr  His  Val  Leu  Leu  Thr  His
1                   5                        10                       15
Thr  Ile  Ser  Arg  Ile
                    20
```

(2) INFORMATION FOR SEQ ID NO:7:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..19
        (D) OTHER INFORMATION: /note= "PEPTIDE 305 (132-150)"

( x i ) SEQUENCE DESCRIPTION: SEQ ID NO:7:

Leu Ser Ala Glu Ile Asn Arg Pro Asp Tyr Leu Asp Phe Ala Glu Ser
1               5                   10                  15

Gly Gln Val ( 2 ) INFORMATION FOR SEQ ID NO:8:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..14
        ( D ) OTHER INFORMATION: /note= "PEPTIDE 306 (13-26)"

( x i ) SEQUENCE DESCRIPTION: SEQ ID NO:8:

Val Ala His Val Val Ala Asn Pro Gln Ala Glu Gly Gln Leu
1               5                   10

( 2 ) INFORMATION FOR SEQ ID NO:9:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note= "PEPTIDE 307 (22-40)"

( x i ) SEQUENCE DESCRIPTION: SEQ ID NO:9:

Ala Glu Gly Gln Leu Gln Trp Leu Asn Arg Arg Ala Asn Ala Leu Leu
1               5                   10                  15

Ala Asn Gly ( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /note= "PEPTIDE 308 (54-68)"

( x i ) SEQUENCE DESCRIPTION: SEQ ID NO:10:

Gly Leu Tyr Leu Ile Tyr Ser Gln Val Leu Phe Lys Gly Gln Gly
1               5                   10                  15

( 2 ) INFORMATION FOR SEQ ID NO:11:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:

(A) NAME/KEY: Peptide
(B) LOCATION: 1..22
(D) OTHER INFORMATION: /note= "PEPTIDE 309 (73-94)"

(xi) SEQUENCE DESCRIPTION: SEQ ID NO:11:

His Val Leu Leu Thr His Thr Ile Ser Arg Ile Ala Val Ser Tyr Gln
1               5                   10                  15

Thr Lys Val Asn Leu Leu
            20

(2) INFORMATION FOR SEQ ID NO:12:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..11
    (D) OTHER INFORMATION: /note= "PEPTIDE 323 (79-89)"

(xi) SEQUENCE DESCRIPTION: SEQ ID NO:12:

Thr Ile Ser Arg Ile Ala Val Ser Tyr Gln Thr
1               5                   10

(2) INFORMATION FOR SEQ ID NO:13:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..9
    (D) OTHER INFORMATION: /note= "PEPTIDE 393 (76-84)"

(xi) SEQUENCE DESCRIPTION: SEQ ID NO:13:

Leu Thr His Thr Ile Ser Arg Ile Ala
1               5

(2) INFORMATION FOR SEQ ID NO:14:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..14
    (D) OTHER INFORMATION: /note= "PEPTIDE 394 (81-94)"

(xi) SEQUENCE DESCRIPTION: SEQ ID NO:14:

Ser Arg Ile Ala Val Ser Tyr Gln Thr Lys Val Asn Leu Leu
1               5                   10

(2) INFORMATION FOR SEQ ID NO:15:

(i) SEQUENCE CHARACTERISTICS:
    (A) LENGTH: 11 amino acids
    (B) TYPE: amino acid
    (D) TOPOLOGY: linear ( i i ) MOLECULE TYPE: peptide ( i x ) FEATURE:
    ( A ) NAME/KEY: Peptide
    ( B ) LOCATION: 1..11
    ( D ) OTHER INFORMATION: /note= "PEPTIDE 395 (70-80)"

( x i ) SEQUENCE DESCRIPTION: SEQ ID NO:15:

Pro Ser Thr His Val Leu Leu Thr His Thr Ile
1              5                          10

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /note= "PEPTIDE 396 (84-94)"

( x i ) SEQUENCE DESCRIPTION: SEQ ID NO:16:

Ala Val Ser Tyr Gln Thr Lys Val Asn Leu Leu
1              5                          10

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /note= "PEPTIDE 418"

( x i ) SEQUENCE DESCRIPTION: SEQ ID NO:17:

Pro Ser Ala His Val Leu Leu Thr His Thr Ile
1              5                          10

( 2 ) INFORMATION FOR SEQ ID NO:18:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /note= "PEPTIDE 419"

( x i ) SEQUENCE DESCRIPTION: SEQ ID NO:18:

Pro Ser Thr His Val Leu Ile Thr His Thr Ile
1              5                          10

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..15
    ( D ) OTHER INFORMATION: /note= "PEPTIDE 462"

( i x ) FEATURE:
    ( A ) NAME/KEY: Modified-site
    ( B ) LOCATION: 5..6
    ( D ) OTHER INFORMATION: /note= "CYS (Acm) PROTECTION PERMANENT"

( x i ) SEQUENCE DESCRIPTION: SEQ ID NO:19:

Lys Gly Gln Gly Cys Pro Ser Thr His Val Leu Leu Thr His Thr
1               5                   10                  15

NEUTROPHIL STIMULATING PEPTIDES

BACKGROUND OF THE INVENTION

This application is a continuation-in-part of U.S. Ser. No. 07/930,415, filed Nov. 9, 1992, now abandoned; which was the national phase filing of priority application PCT/AU 91/00086, filed Mar. 12, 1991, published as WO 91/13908 on 19 Sep. 1991; which claimed priority to Australian patent application PJ 9065, filed Mar. 12, 1990.

The present invention relates to peptides having neutrophil stimulating activity, and to use of these peptides as therapeutic agents.

Tumour necrosis factor (TNF) was first identified as a factor found in the serum of Bacillus Calmette-Guerin treated mice which caused haemorrhagic regression of certain transplanted tumours and had cytolytic activity on several transformed cell lines vitro (Carswell et al, PNAS 72, 3666–3670; Helson et al, 1975, Nature 258, 731–732). TNF, a product of activated macrophages, has subsequently been shown to be a primary mediator in the pathology of endotoxic shock (Tracey et al 1986, Science 234, 470–474). In addition to its pathological effects TNF also has a central role in host defences against viral, bacterial and parasitic pathogens.

The cellular targets of TNF important in host defence include neutrophils, eosinophils, monocyte/macrophages and lymphocytes. Within this context TNF is a major mediator of neutrophil activation. TNF stimulates enhanced phagocytosis (Shalaby et al 1985, J.Immunol., 135, 2069-2073), enhanced production of superoxide anions (Teujiimoto et al, 1986, Biochem. Biophys. Res. Commun., 137 1094–1100), release of lysozyme and hydrogen peroxide and causes neutrophil degranulation (Klebanoff et al, 1986, J.Immunol., 136, 4220–4225). Neutrophils also show enhanced microbiocidal and tumouricidal activity when stimulated by TNF (Shalaby et al, 1985, J.Immunol., 135, 2069–2073; Djeu et al, 1986, J.Immunol., 137, 2980–2984; Blanchard et al, 1989, J. Leuk. Biol., 45, 538–545). It has been hypothesized that the cytostatic effect of TNF is mediated by high local concentrations of hydrogen peroxide produced by neutrophils (Shau 1986, J.Immunol., 141, 234–240).

TNF pretreatment enhances the response of neutrophils to N-formyl-L-methionyl-L-leucyl-L-phenylalanine (F-met-leu-phe) and phorbol myristate acetate through specific receptors (Ferrante et al 1988, Int. Arch. Allergy Appl. Immunol., 86, 82–91). Neutrophils accumulate at sites of inflammation, caused in part by the increased expression of complement receptors by TNF (Berger et al 1988, Blood 71, 151–158). Further TNF causes neutrophil emigration into skin (Cybulsky et al 1988, J. Immunol. 140, 3144–3149).

Neutrophil function is known to be depressed in a number of viral, bacterial and parasitic infections (Abramson and Mills, 1988, Rev. Infect. Dis., 10, 326–341; Ferrante et al, 1989, Immunol. Letts., 22, 301–6). Depressed neutrophil function has, for example, been described in Acquired Immune Deficiency Syndrome (Thorsen et al, 1989, AIDS, 3, 651–653; Ellis et al, 1988, J. Infect. Dis., 158, 1268–1276; Murphy et al, 1988, J. Infect. Dis., 158, 627–630). Clearly TNF, which appears to play an important role in neutrophil activation both in vitro and in vivo as described above, given exogenously has the potential to overcome these neutrophil defects. The administration of TNF or indeed overproduction of TNF is, however, associated with severe side effects and the manifestation of pathology such as thrombocytopaenia, lymphocytopaenia, hepatotoxicity, renal impairment and hypertension.

SUMMARY OF THE INVENTION

The present inventors have identified novel peptides derived from the primary amino acid sequence of human TNF which stimulate neutrophil activity. These peptides have indicated that the region of amino acids 54 to 94 of human TNF has previously undiscovered neutrophil stimulating activity. This observation has important clinical applications as treatment with such peptides would be expected to restore depressed or aberrant neutrophil activity, but would not be expected to cause the severe side effects associated with the therapeutic use of the whole TNF molecule.

DETAILED DESCRIPTION OF THE INVENTION

Accordingly, in a first aspect the present invention consists in a peptide which primes neutrophils for superoxide production and an enhanced respiratory burst following treatment with N-formyl-L-methionyl-L-leucyl-L-phenylalanine, wherein the peptide is of the general formula:

$X_1$—$X_2$—$X_3$—$X_4$—$X_5$—$X_6$—$X_7$ in which
$X_1$ is null, Cys or $R_1$
$X_2$ is null, Cys, R1, or A1-A2-A3-A4-A5-A6-A7 in which
  A1 is Leu, Ile, Val or Met
  A2 is Phe, Tyr, Trp or His
  A3 is Lys, Arg or His
  A4 is Gly or Ala
  A5 is Gln or Asn
  A6 is Gly or Ala
  A7 is Cys
$X_3$ is Cys, R1 or A8-A9-A10
in which
  A8 is Pro or Nα-alkylamino acid
  A9 is Ser or Thr
  A10 is Thr or Ser or Ala or Gly
$X_4$ is A11-A12-A13-A14-A15-A16-A17-A18
in which
  A11 is His, Lys or Arg
  A12 is Val, Ile, Leu or Met
  A13 is Leu, Ile Val or Met
  A14 is Ile, Leu, Val or Met
  A15 is Thr or Ser
  A16 is His, Lys or Arg
  A17 is Thr or Ser
  A18 is 16, Leu, Val or Met
$X_5$ is Cys, R2 or A19-A20-A21
in which
  A19 is Ser or Thr
  A20 is Arg, Lys or His
  A21 is Ile, Leu, Val or Met
$X_6$ is null, Cys, R2 or A22-A23-A24-A25-A26-A27-A28-A29-A30-A31-A32
in which
  A22 is Ala or Gly
  A23 is Val, Ile, Leu or Met
  A24 is Ser or Thr
  A25 is Tyr, Phe, Trp or His A26 is Glu or Asp A27 is Thr or Ser A28 is Lys, Arg or His A29 is Val, Ile, Leu or Met A30 is Asn or Gln A31 is Leu, Ile, Val or Met A32 is Leu, Ile, Val or Met X7 is null, Cys or R2

R1 is H or R-CO, where R is H, straight, branched or cyclic alkyl up to C20, optionally containing double bonds and/or substituted with halogen, nitro, amino, hydroxy, sulfo, phospho or carboxyl groups which may be substituted themselves or aralkyl or aryl optionally substituted as listed for the alkyl or R1 is glycosyl, nucleosyl or lipoyl and R1 is absent when the amino acid adjacent is an unsubstituted desamino-derivative;

R2 is -NR12R13, wherein R12 and R13 are independently H, straight, branched or cyclic alkyl, aralkyl or aryl optionally substituted as defined for R1 or R2 is N-glycosyl or N-lipoyl, or R2 is —OR14, where R14 is H straight, branched or cyclic alkyl, aralkyl or aryl, optionally substituted as defined for R1 or R2 is -0- glycosyl, or -0- lipoyl or R2 is absent when the adjacent amino acid is a dicarboxy derivative of cysteine or a homologue thereof or the peptide is in a N-C cyclic form, with the proviso that:

X1 is always and only null when X2 is R1, Cys or null

X2 is always and only null when X3 is R1 or Cys

X6 is always and only null when X5 is R2 or Cys

X7 is always and only null when X6 is R2 or Cys or null.

In a preferred embodiment of the present invention X1 is null, X2 is R1, X3 is A8-A9-A10, X5 is R2 and X6 and X7 are null. It is further preferred that A8 is Pro, A9 is Ser, A10 is Thr, A11 is His, A12 is Val, A13 is Leu, A14 is Leu, A15 is Thr, A16 is His, A17 is Thr and A18 is Ile, or A8 is Pro, A9 is Ser, A10 is Thr, A11 is His, A12 is Val, A13 is Leu, A14 is Ile, A15 is Thr, A16 is His, A17 is Thr and A18 is Ile, or A8 is Pro, A9 is Ser, A10 is Ala, A11 is His, A12 is Val, A13 is Leu, A14 is Leu, A15 is Thr, A16 is His, A17 is Thr and A18 is Ile.

In another preferred embodiment of the present invention X1 is R1, X2 is A1-A2-A3-A4-A5-A6-A7, X3 is A8-A9-A10, X5 is A19-A20-A21, X6 is R2 and X7 is null. It is further preferred that A1 is Leu, A2 is Phe, A3 is Lys, A4 is Gly, A5 is Gln, A6 is Gly, A7 is Cys, A8 is Pro, A9 is Ser, A10 is Thr, A11 is His A12 is Val, A13 is Leu, A14 is Leu, A15 is Thr, A16 is His, A17 is Thr, A18 is Ile, A19 is Ser, A20 is Arg and A21 is Ile.

In yet another preferred embodiment of the present invention X1 and X2 are null, X3 is R1, X5 is A19-A20-A21, X6 is A22-A23-A24-A25-A26-A27-A28-A29-A30-A31-A32 and X7 is R2. It is further preferred that A11 is His, A12 is Val, A13 is Leu, A14 is Leu, A15 is Thr, A16 is His A17 is Thr, A18 is Ile, A19 is Ser, A20 is Arg, A21 is Ile, A22 is Ala, A23 is Val, A24 is Val, A25 is Ser, A26 is Tyr, A27 is Glu, A28 is Lys, A29 is Val, A30 is Asa, A31 is Leu and A32 is Leu.

In a second aspect the present invention consists in a peptide which primes neutrophils for superoxide production and an enhanced respiratory burst following treatment with N-formyl-L-methionyl-L-leucyl-L-phenylalanine, wherein the peptide is of the general formula:

B1 —Y1 —Y2—Y3—Y4—Y5—Y6—Y7—Y8—Y9—Y10—Y11—Y12—Y13—Y14—Y15—B2 in which

Y1 is Gly or Ala

Y2 is Leu or Ile or Val or Met

Y3 is Tyr or Phe or Trp or His

Y4 is Leu or Ile or Val or Met

Y5 is Ile or Leu or Val or Met

Y6 is Tyr or Phe or Trp or His

Y7 is Ser or Thr

Y8 is Gln or Asn

Y9 is Val or Ile or Leu or Met

Y10 is Leu or Val or Ile or Met

Y11 is Phe or Tyr or Trp or His

Y12 is Lys or Arg or His

Y13 is Gly or Ala

Y14 is Asn or Gln

Y15 is Gly or Ala

B1 is H or R-CO, where R is H, straight, branched or cyclic alkyl up to C20, optionally containing double bonds and/or substituted with halogen, nitro, amino, hydroxy, sulfo, phospho or carboxyl groups (which may be substituted themselves or aralkyl or aryl optionally substituted as listed for the alkyl or B1 is glycosyl, nucleosyl or lipoyl and B1 is absent when the amino acid adjacent is an unsubstituted desamino-derivative; B2 is —NR12R13, wherein R12 and R13 are independently H, straight, branched or cyclic alkyl, aralkyl or aryl optionally substituted or defined for B1 or B2 is N-glycosyl or N-lipoyl, or B2 is —OR14, where R14 is H straight, branched or cyclic alkyl, aralkyl or aryl, optionally substituted as defined for B1 or B2 is -0- glycosyl, or -0- lipoyl or B2 is absent when the adjacent amino acid is a dicarboxy derivative of cysteine or a homologue thereof or the peptide is in a N-C cyclic form.

As will be appreciated by those skilled in the art from the description which follows the present inventors have demonstrated that the region of human TNF from amino acid 54 to amino acid 94 plays an important functional role in the stimulation of neutrophils. Further, the present inventors have produced 6 peptides namely peptides 304, 308, 309, 395, 418 and 419 (as referred to herein) which have neutrophil stimulating activity.

Armed with this information and with the aid of co-ordinates of the crystalline structure of TNF at 2.6 A as disclosed by Eck and Sprang, 1989 (J. Biol. Chem., 264: 18795–17605), the person skilled in the art will be able to design non-peptide structures which, in 3 dimensional terms mimic the peptides of the present invention. It is believed that these non-peptide structures will also mimic the physiological effects of the peptides of the present invention. It is intended that such non-peptide structures are included within the scope of the present invention. Changes to the TNF molecule in these regions using e.g. site directed mutagenesis would also be expected to affect neutrophil activation. A schematic representation of the three dimensional structure of TNFα is shown in FIG. 8.

Accordingly in a third aspect the present invention consists in a compound the three dimensional structure of which substantially corresponds to the three dimensional structure of the peptide of the first or second aspects of the present invention, the compound being characterized in that the compound is capable of eliciting superoxide production by neutrophils and of priming neutrophils for an enhanced respiratory burst following treatment with N-formyl-L-methionyl-L-leucyl-L-phenylalanine.

In a further aspect, the present invention consists in a method of treating a subject having depressed neutrophil function, the method comprising administering to the subject a therapeutic amount of the peptide of the first aspect of the present invention.

In a preferred embodiment of this aspect of the present invention the subject is suffering from acquired immune deficiency syndrome.

Peptide 308, [SEQ ID NO. 101] through selective effects on neutrophil degranulation may be administered to individuals suffering from inflammatory syndromes e.g. rheumatoid arthritis, adult respiratory distress syndrome.

It will be appreciated by those skilled in the art that a number of modifications may be made to the peptide of the present invention without deleteriously effecting the biological activity of the peptide. This may be achieved by various changes, such as insertions, deletions and substitutions (e.g., sulfation, phosphorylation, nitration, halogenation), either conservative or non-conservative (e.g., W-amino acids, desamino acids) in the peptide sequence where such changes do not substantially altering the overall biological activity of the peptide. By conservative substitutions the intended combinations are:

G, A; V, I, L, M; D, E; N, Q; S, T; K, R, H; F, Y, W, H; and P, Nα-alkylamino acids.

It may also be possible to add various groups to the peptide of the present invention to confer advantages such as increased potency or extended half-life in vivo, without substantially altering the overall biological activity of the peptide.

The term peptide is to be understood to embrace peptide bond replacements and/or peptide mimetics, i.e. pseudopeptides, as recognised in the art (see for example: Proceedings of the 20th European Peptide Symposium, edt. G. Jung. E. Bayer, pp. 289–336, and references therein), as well as salts and pharmaceutical preparations and/or formulations which render the bioactive peptide(s) particularly suitable for oral, topical, nasal spray, ocular pulmonary, I.V., subcutaneous, as the case may be, delivery. Such salts, formulations, amino acid replacements and pseudopeptide structures may be necessary and desirable to enhance the stability, formulation, deliverability (e.g., slow release, prodrugs), or to improve the economy of production, and they are acceptable, provided they do not negatively affect the required biological activity of the peptide.

Apart from substitutions, three particular forms of peptide mimetic and/or analogue structures of particular relevance when designating bioactive peptides, which have to bind to a receptor while risking the degradation by proteinases and peptidases in the blood, tissues and elsewhere, may be mentioned specifically, illustrated by the following examples: Firstly, the inversion of backbone chiral centres leading to D-amino acid residue structures may, particularly at the N-terminus, lead to enhanced stability for proteolytical degradation while not impairing activity. An example is given in the paper "Tritriated D-ala$^1$-Peptide T Binding", Smith, C. S. et al, Drug Development Res. 15, pp. 371–379 (1988). Secondly, cyclic structure for stability, such as N to C interchain imides and lactames (Ede et al in Smith and Rivier (Eds) "Peptides: Chemistry and Biology", Escom, Leiden (1991), p268–270), and sometimes also receptor binding may be enhanced by forming cyclic analogues. An example of this is given in "Confirmationally restricted thymopentin-like compounds", U.S. Pat. No. 4,457,489 (1985), Goldstein, G. et al. Finally, the introduction of ketomethylene, methylsulfide or retroinverse bonds to replace peptide bonds, i.e. the interchange of the CO and NH moieties may both greatly enhance stability and potency. An example of the latter type is given in the paper "Biologically active retroinverse analogues of thymopentin", Sisto A. et al in Rivier, J. E. and Marshall, G. R. (eds.) "Peptides, Chemistry, Structure and Biology", Escom, Leiden (1990), p.722–773.

The peptides of the invention can be synthesized by various methods which are known in principle, namely by chemical coupling methods (cf. Wunsch, E.: "Methoden der organischen Chemie", Volume 15, Band 1+2, Synthese von Peptiden, Thieme Verlag, Stuttgart (1974), and Barrany, G.;

Merrifield, R. B: "The Peptides", eds. E. Gross, J. Meienhofer., Volume 2, Chapter 1, pp. 1–284, Academic Press (1980)), or by enzymatic coupling methods (cf. Widmer, F., Johansen, J. T., Carlsberg Res. Commun., Volume 44, pp. 37–46 (1979), and Kullmann, W.: "Enzymatic Peptide Synthesis", CRC Press Inc., Boca Raton, Fla. (1987), and Widmer, F., Johansen, J. T. in "Synthetic Peptides in Biology and Medicine:", eds., Alitalo, K., Partanen, P., Vatieri, A., pp. 79–86, Elsevier, Amsterdam (1985)), or by a combination of chemical and enzymatic methods if this is advantageous for the process design and economy.

It will be seen that one of the alternatives embraced in the general formula set out above is for a cysteine residue to be positioned at both the amino and carboxy terminals of the peptide. This will enable the cyclisation of the peptide by the formation of di-sulphide bond.

It is intended that such modifications to the peptide of the present invention which do not result in a decrease in biological activity are within the scope of the present invention.

As would be recognized by those skilled in the art there are numerous examples to illustrate the ability of anti-idiotypic (anti-Ids) antibodies to an antigen to function like that antigen in its interaction with animal cells and components of cells. Thus, anti-Ids to a peptide hormone antigen can have hormone-like activity and interact specifically with the receptors to the hormone. Conversely, anti-Ids to a receptor can interact specifically with a mediator in the same way as the receptor does. (For a review of these properties see: Gaulton, G. N. and Greane, M. I. 1986. Idiotypic mimicry of biological receptors, Ann. Rev. Immunol. 4, 253–280; Sege, K and Peterson, P. A., 1978. Use of anti-idiotypic antibodies as cell surface receptor probes. Proc. Natl. Acad. Sci. U.S.A. 75, 2443–2447).

As might be expected from this functional similarity of anti-Id and antigen, anti-Ids bearing the internal image of an antigen can induce immunity to such an antigen. (This nexus is reviewed in Hiernaux, J. R. 1988. Idiotypic vaccines and infectious diseases. Infect. Immun. 56, 1407–1413.)

As will be appreciated by persons skilled in the art from the disclosure of this application it will be possible to produce anti-idiotypic antibodies to the peptide of the present invention which will have similar biological activity. It is intended that such anti-idiotypic antibodies are included within the scope of the present invention.

Accordingly, in a fourth aspect the present invention consists in an anti-idiotypic antibody to the peptide of the first aspect of the present invention, the anti-idiotypic antibody being capable of inducing macrophage and/or neutrophil activation.

The individual specificity of antibodies resides in the structures of the peptide loops making up the Complementary Determining Regions (CDRs) of the variable domains of the antibodies. Since in general, the amino acid sequences of the CDR peptide loops of an anti-Id are not identical to or even similar to the amino acid sequence of the peptide antigen from which it was originally derived, it follows that peptides whose amino acid sequence is quite dissimilar, in certain contexts can take up a very similar three-dimensional structure. The concept of this type of peptide, termed a "functionally equivalent sequence" or mimotope by Geyson is familiar to those expert in the field. (Geyson, H. M. et al 1987. Strategies for epitope analysis using peptide synthesis. J. Immun. Methods. 102, 259–274).

Moreover, the three-dimensional structure and function of the biologically active peptides can be simulated by other compounds, some not even peptidic in nature, but which mimic the activity of such peptides. This field of science is summarised in a review by Goodman, M. (1990). (Synthesis, spectroscopy and computer simulations in peptide research. Proc. 11th American Peptide Symposium published in *Peptide-Chemistry, Structure and Biology pp 3–29.* Ed Rivier, J. E. and Marshall, G. R. Publisher ESCOM.)

As will be recognized by those skilled in the art, armed with the disclosure of this application, it will be possible to produce peptide and non-peptide compounds having the same three-dimensional structure as the peptide of the present invention. These "functionally equivalent structures" or "peptide mimics" will react with antibodies raised against the peptide of the present invention and may also be capable of stimulating macrophages and/or neutrophils. It is intended that such "peptide mimics" are included within the scope of the present invention.

Accordingly, in a fifth aspect the present invention consists in a compound the three-dimensional structure of which is similar as a pharmacophore to the three- dimensional structure of the peptide of the first aspect of the present invention, the compound being characterized in that it reacts with antibodies raised against the peptide of the first aspect of the present invention and that the compound is capable of activating macrophages and/or neutrophils.

More detail regarding pharmacophores can be found in Bolin et al. p 150, Polinsky et al. p 287, and Smith et al. p 485 in Smith and Rivier (Eds) "Peptides: Chemistry and Biology", Escom, Leiden (1991).

As will be appreciated by those skilled in the art the peptides of the present invention will bind to the TNF receptor. Accordingly, the peptides of the present invention can be used in assays for the presence of TNF receptor in samples. These samples may be either biological fluids or tissue sections. When used in this manner it is preferred that the peptides are labelled with a detectable label.

In order that the nature of the present invention may be more clearly understood, preferred forms thereof will now be described with reference to the following examples, and Figures in which:

BRIEF DESCRIPTION OF THE DRAWINGS

FIG. 1 shows the amino acid sequence of human TNF; [SEQ ID NO. 1]

Figure 2:
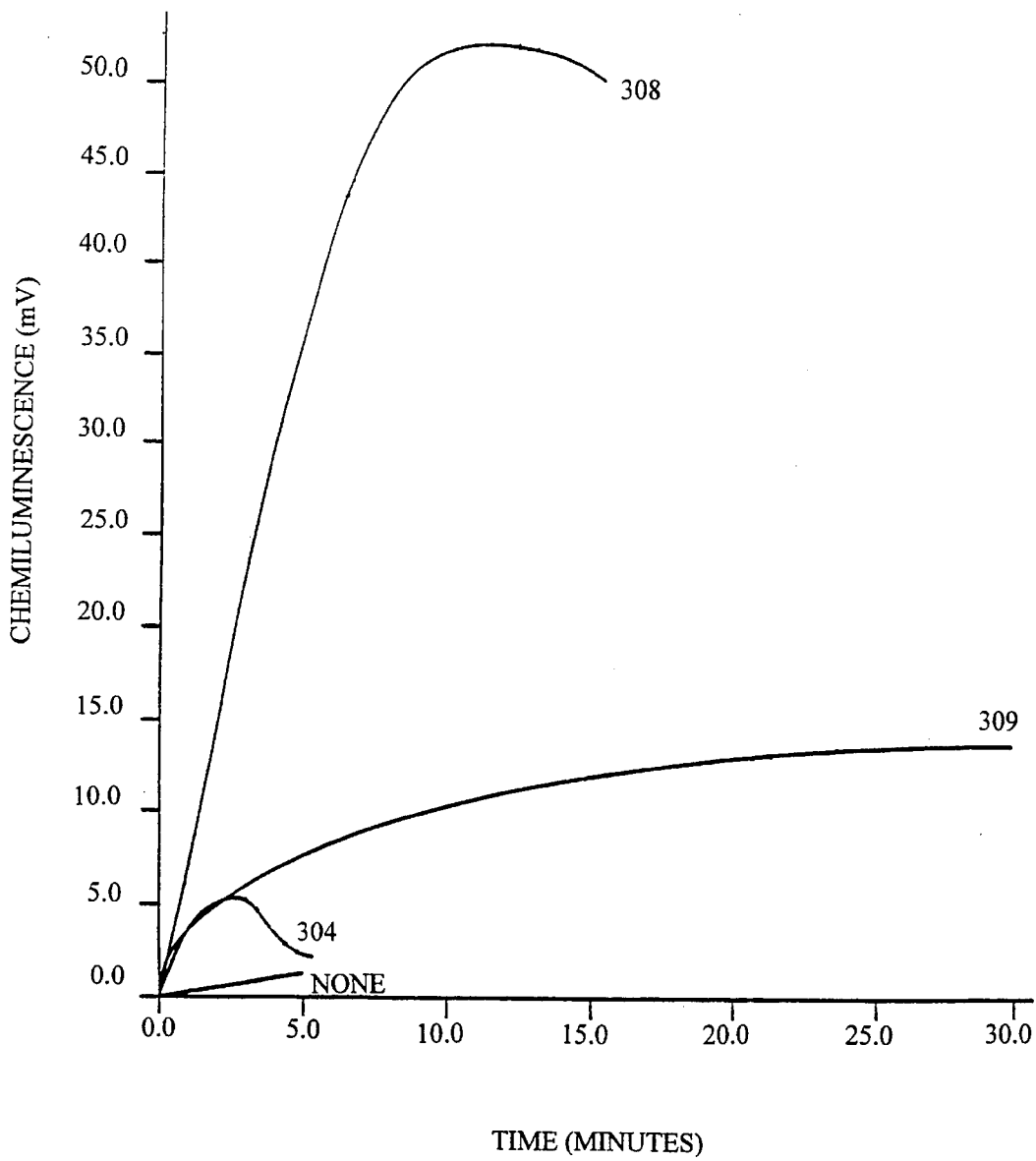
FIG. 2 shows the effects of peptides 304 [SEQ ID NO. 6] (o), 308 [SEQ ID NO. 10] (□) and 309 [SEQ ID NO. 11] (Δ) on the fMLP induced human neutrophil response. Peptides were used at 100 µg/$10^5$ in the 20 min pre-incubation step.

Production of human TNF peptides tested for neutrophils stimulatory activity

The following peptides were synthesised and are described using the I.U.P.A.C. one-letter code abbreviations for amino acid residues with the TNF sequence region indicated in brackets.

Peptide 275
A K P W Y E P I Y L (111–120) [SEQ ID NO. 2]
Peptide 301
V R S S S R T P S D K P V A H V V A (1–18) [SEQ ID NO. 3]
Peptide 302
L R D N Q L V V P S E G L Y L I (43–58) [SEQ ID NO. 4]
Peptide 303
L S A I K S P C Q R E T P E G A (94–109) [SEQ ID NO. 5]
Peptide 304
L F K G Q G C P S T H V L L T H T I S R I (63–83) [SEQ ID NO. 6]
Peptide 305
L S A E I N R P D Y L D F A E S G Q V (132–150) [SEQ ID NO. 7]
Peptide 306
V A H V V A N P Q A E G Q L (13–26) [SEQ ID NO. 8]
Peptide 307
A E G Q L Q W L N R R A N A L L A N G (22–40) [SEQ ID NO. 9]
Peptide 308
G L Y L I Y S Q V L F K G Q G (54–68) [SEQ ID NO. 10]
Peptide 309
H V L L T H T I S R I A V S Y Q T K V N L L (73–94) [SEQ ID NO. 11]
Peptide 323
T I S R I A V S Y Q T (79–89) [SEQ ID NO. 12][SEQ ID NO. 12]
Peptide 393
L T H T I S R I A (76–84). [SEQ ID NO. 13]
Peptide 394
S R I A V S Y Q T K V N L L (81–94). [SEQ ID NO. 14]
Peptide 395
P S T H V L L T H T I (70–80). [SEQ ID NO. 15]
Peptide 396
A V S Y Q T K V N L L (84–94). [SEQ ID NO. 16]
Peptide 418
P S A H V L L T H T I [SEQ ID NO. 17]
Peptide 419
P S T H V L I T H T I [SEQ ID NO. 18]
Peptide 462
K G Q G Cys (Acm) P S T H V L L T H T [SEQ ID NO. 19]

These peptides were synthesised using the following general protocol.

All peptides were synthesised using the Fmoc-polyamide method of solid phase peptide synthesis (Atherton et al, 1978, J. Chem. Soc. Chem. Commun., 13, 537–539), The solid resin used was PepSyn KA which is a polydimethyacrylamide gel on kieselguhr support with 4-hydroxymethylphenoxyacetic acid as the functionalised linker (Atherton et al, 1975, J. Am. Chem. Soc., 97, 6584–6585).

The carboxy terminal amino acid is attached to the solid support by a DCC/DMAP-mediated symmetrical-anhydride esterification.

All Fmoc-groups are removed by piperidine/DMF wash and peptide bonds are formed either via pentafluorophenyl active esters or directly by BOP/NMM/HOBt (Castro's reagent) except for certain amino acids as specified in Table 1.

Side chain protection chosen for the amino acids are removed concomitantly during cleavage with the exception of Acm on cysteine which is left on after synthesis

TABLE 1

| Amino acid | Protecting group | Coupling Method |
|---|---|---|
| Arg | Mtr or Pmc | Either |
| Asp | OBut | Either |
| Cys | Acm (permanent) | Either |
| Glu | OBut | Either |
| His | Boc | OPfp only |
| Lys | Boc | Either |
| Ser | But | BOP only |
| Thr | But | BOP only |
| Tyr | But | Either |
| Asn | none | OPfp only |
| Gln | none | OPfp only |

Cleavage and Purification

Peptide 302. [SEQ ID NO. 4] Peptide is cleaved from the resin with 95% TFA and 5% thioanisole (1.5 h) and purified on reverse phase C4 column. (Buffer A—0.1% aqueous TFA, Buffer B—80% ACN 20% A)

Peptide 304. [SEQ ID NO. 6] Peptide is cleaved from the resin with 95% TFA and 5% phenol (5 h) and purified on reverse phase C4 column. (Buffer A—0.1% aqueous TFA, Buffer B—80% ACN 20% A).

Peptide 308. [SEQ ID NO. 10] Peptide is cleaved from the resin with 95% TFA and 5% water (1.5 h) and purified on reverse phase C4 column. (Buffer A—0.1% aqueous TFA, Buffer B—80% ACN 20% A).

Peptide 309. [SEQ ID NO. 11] Peptide is cleaved from the resin with 95% TFA and 5% thioanisole and purified on reverse phase C4 column. (Buffer A—0.1% aqueous TFA, Buffer B—80% ACN 20% A).

Effect of TNF peptides on neutrophil function

Chemiluminescence assay

This assay examined the effect of TNF peptides on priming for a neutrophil F-met-leu-phe response as described by Ferrante et al, 1988, (Int. Arch. Allergy Appl. Immunol, 86, 82–91). Purified human neutrophils were pretreated with peptide for 20 minutes before the addition of f-met-leu-phe. The lucigenin dependent chemiluminescence response, which reflects superoxide production, was then measured. The results obtained are set out in Table 2 and are expressed as mV of lucigenin dependent chemiluminescence and represent the maximal cell activity attained.

In addition, the effects of peptide 304,308 and 309 [SEQ ID NOS. 6, 10, 11] are shown graphically in FIG. 2.

This experiment was repeated with peptides 304, 308 and 309 [SEQ ID NOS. 6, 10, 11] The results obtained as shown in Table 3.

Figure 3:
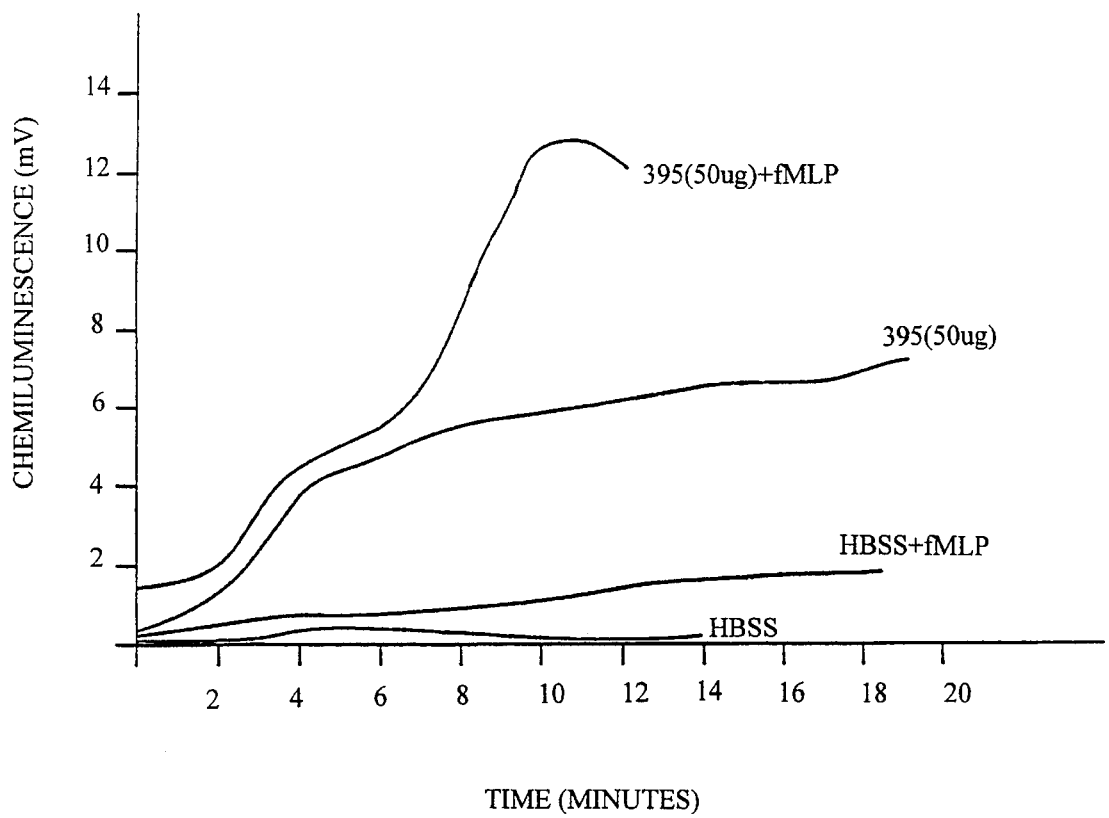
FIG. 3 shows the kinetics of the chemiluminescence response elicited by Peptide 395 [SEQ ID NO. 15] (●—●; 395 (50 µg)+fMLP; ■—■; 395 (50 µg): HBSS+fMLP; O—OHBSS)

The experiment was also conducted using peptides 393, 394, 395 and 396. [SEQ ID NOS. 13, 14, 15, 16] Of these peptides only peptide 395 [SEQ ID NO. 15] was able to stimulate the neutrophil respiratory burst (Table 4). The effect of peptide 395 was dose dependent as shown by the results of 3 experiments (Table 5). The kinetics of the chemiluminescence response elicited by peptide 395 is shown in FIG. 3. Peptide 395 displays improved solubility over peptide 309.

TABLE 2

| | Concentration μg/10⁶ cells) | | | | |
|---|---|---|---|---|---|
| Peptide | 0 | 1 | 10 | 100 | 500 |
| 275 [SEQ ID NO. 2] | 1.02 | 0.99 | 0.69 | 0.43 | 0.80 |
| 301 [SEQ ID NO. 3] | 0.34 | 0.93 | 0.74 | 0.55 | 1.10 |
| 302 [SEQ ID NO. 3] | 0.37 | 0.16 | 0.18 | 0.29 | |
| 303 [SEQ ID NO. 4] | 0.37 | 0.23 | 0.17 | 0.22 | |
| 304 [SEQ ID NO. 5] | 0.37 | 0.18 | 0.43 | 2.56 | 2.76 |
| 305 [SEQ ID NO. 6] | 0.37 | 0.27 | 0.36 | 0.24 | |
| 306 [SEQ ID NO. 7] | 0.37 | 0.27 | 0.35 | 0.23 | |
| 307 [SEQ ID NO. 8] | 0.37 | 0.35 | 0.37 | 0.42 | |
| 323 [SEQ ID NO. 12] | 0.37 | 0.23 | 0.17 | 0.47 | |
| 308 [SEQ ID NO. 10] | 0.37 | 0.91 | 4.80 | 49.52 | |
| 309 [SEQ ID NO. 11] | 0.37 | 0.38 | 0.98 | 13.44 | |

Results are expressed as mV of lucigenin dependent chemiluminescence and represent peak of response i.e. the maximal cell activity attained.

TABLE 3

| | Peptide concentration (μg/10⁶ cells) | | |
|---|---|---|---|
| Peptide | 0 | 10 | 100 |
| 304 [SEQ ID NO. 6] | 0.04 | 0.36 | 0.64 |
| 304 + fMLP | 0.71 | 0.91 | 6.97 |
| 308 [SEQ ID NO. 10] | 0.04 | 1.00 | 11.76 |
| 308 + fMLP | 0.42 | 2.74 | 28.56 |
| 309 [SEQ ID NO. 11] | 0.04 | 0.31 | 0.69 |
| 309 + fMLP | 0.42 | 2.46 | 12.84 |

TABLE 4

Comparisons of 309 and its subpeptides on neutrophil respiratory burst

| Treatment (100 ug peptide) | Chemiluminescence (mV) |
|---|---|
| Diluent | 0.58 |
| 309 [SEQ ID NO. 11] | 4.70 |
| 393 [SEQ ID NO. 13] | 0.31 |
| 394 [SEQ ID NO. 14] | 0.33 |
| 395 [SEQ ID NO. 15] | 5.32 |
| 396 [SEQ ID NO. 16] | 0.70 |

TABLE 5

Effect of 395 on neutrophil respiratory burst

| | Chemiluminescence (mV) | | |
|---|---|---|---|
| Treatment | Exp. 1 | Exp. 2 | Exp. 3 |
| Diluent | 0.58 | 0.68 | 0.38 |
| fMLP | 1.53 | 3.53 | 1.96 |
| 1 μg 395 [SEQ ID NO. 15] | 3.25 | 0.89 | 0.03 |
| 1 μg 395 + fMLP | 3.36 | 4.55 | 0.29 |
| 10 μg 395 | 4.92 | 3.97 | 0.64 |
| 10 μg 395 + fMLP | 7.31 | 9.10 | 2.34 |
| 50 μg 395 | 8.01 | 10.81 | |
| 50 μg 395 + fMLP | 12.58 | 22.09 | |
| 100 μg 395 | 2.36 | 19.14 | 5.26 |
| 100 μg 395 + fMLP | 5.29 | 18.10 | 10.59 |

TABLE 5-continued

Effect of 395 on neutrophil respiratory burst

| | Chemiluminescence (mV) | | |
|---|---|---|---|
| Treatment | Exp. 1 | Exp. 2 | Exp. 3 |
| 100 μg 309 [SEQ ID NO. 11] | 5.98 | 6.68 | 1.24 |
| 100 μg 309 + fMLP | 27.44 | 22.77 | 6.69 |

Effect on Superoxide Formation

The effect of peptides 308 and 309 [SEQ ID NOS. 10, 11] on superoxide formation was examined by the cytochrome reduction assay, according to the procedure of Ferrante, 1989 (Infection and Immunity), 57: 2115–2122). The results, expressed as n moles of $O_2/5\times10^5$ cells as set out in Table 6.

TABLE 6

| | Peptide concentration ($\mu g/5 \times 10^5$ cells) | | |
|---|---|---|---|
| Peptide | 0 | 10 | 100 |
| 308 [SEQ ID NO. 10] | 0.270 | 2.78 | 4.892 |
| 308 + fMLP | 2.757 | 5.00 | 6.729 |
| 309 [SEQ ID NO. 11] | 0.270 | 0.62 | 2.30 |
| 309 + fMLP | 2.757 | 3.87 | 5.14 |

Figure 4:
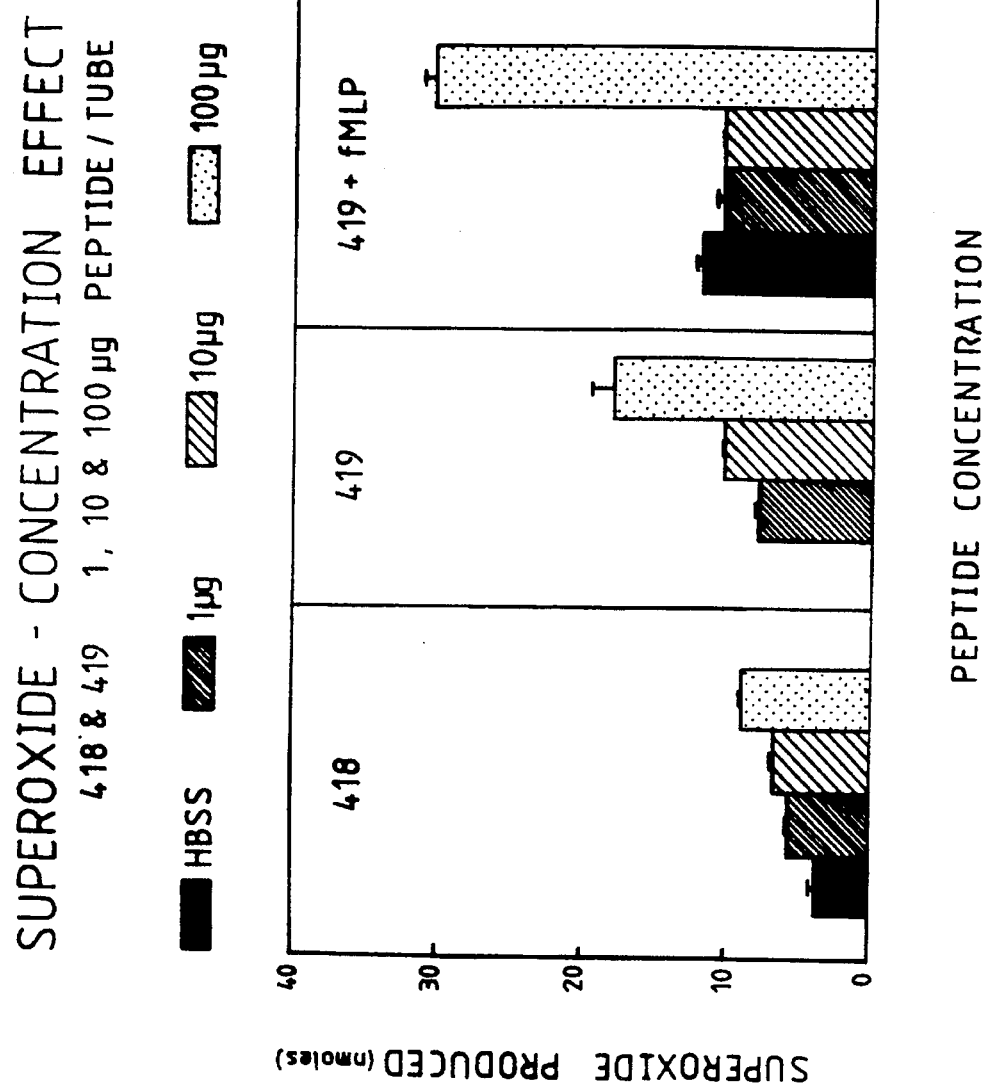
FIG. 4 shows stimulation of superoxide production by peptides 418 and 419; [SEQ ID NOS. 17 & 18]

The effects of peptides 418 and 419 [SEQ ID NOS. 17, 18] or superoxide formation were also assessed in a like manner and the results shown in FIG. 4.

Effect of TNF peptides on the ability of neutrophils to inhibit in vitro growth of malaria parasites It is known that neutrophils stimulated by TNF are able to inhibit the in vitro growth of malaria parasites. The ability of neutrophils stimulated with peptides 418 and 419 [SEQ ID NOS. 17, 18] to inhibit in vitro growth of malaria parasites was assessed.

Briefly, neutrophils were incubated with peptides 418 and 419 [SEQ ID NOS. 17, 18] at 37° C. for 30 minutes and then washed with HBSS. The neutrophils were then added to a culture of red blood cells infected with *P. falciparum*. The cultures were then examined microscopically for evidence of parasite death.

Figure 5:
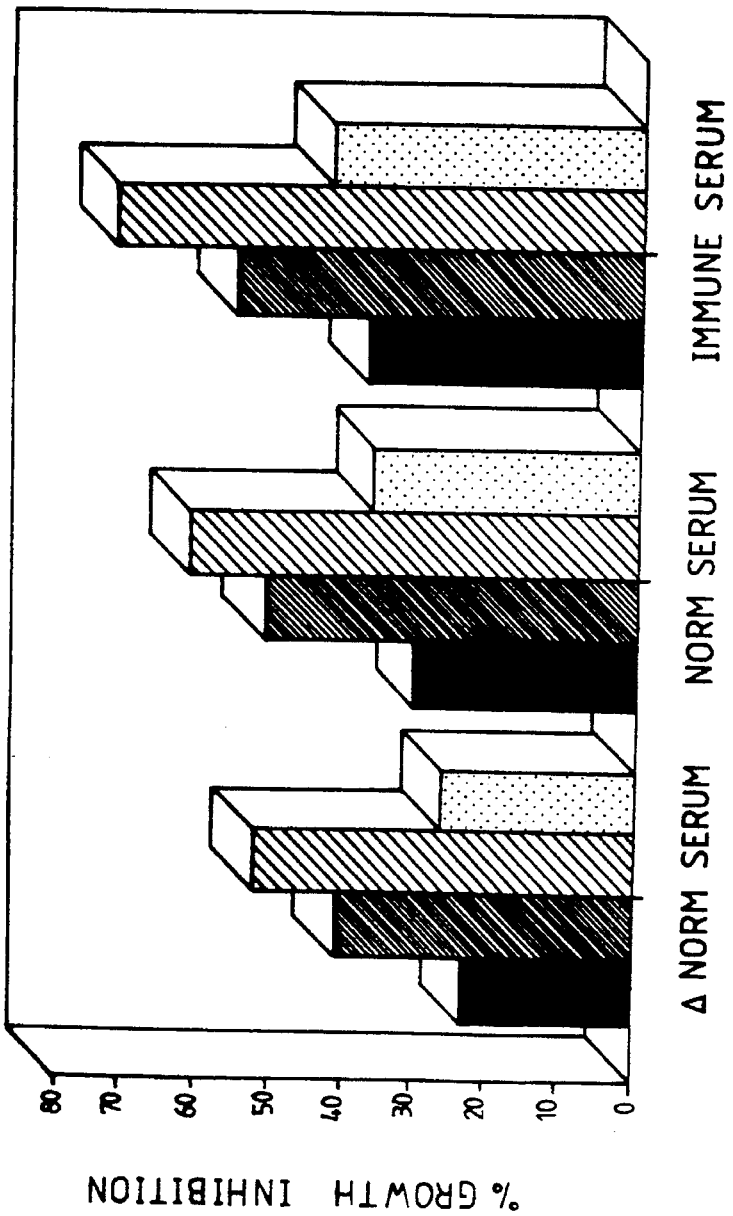
FIG. 5 shows inhibition of in vitro growth of malarial parasites by neutrophils stimulated by either peptide 418 or peptide 419; [SEQ ID NOS. 17 & 18]

The results obtained with thawed normal serum, normal serum and immune serum are shown in FIG. 5. As can be seen peptide 419 [SEQ ID NOS. 18] is more effective than TNF.

BCG Experiment

Peptide 419 [SEQ ID NOS. 18] was tested for the capacity to induce early activation of monocytes leading to reduced infective load and granuloma formation. C57BL/6 ($H_2$) in groups of six mice were infected with *M. bovis* (BCG), $10^7$cfu, by intraperitoneal injection. On days 1, 3, 5, 7 and 9, the mice receive by intravenous injection:

(a) Peptide 419, [SEQ ID NOS. 18] 500 μg in 0.5 ml PBS, (b) TNF, murine recombinant $10^4$ units in 0.5 ml PBS (TNF at this concentration has been shown to be non-toxic in mice; Longermans et al Infection & Immunity, 1992, 60:5107–5112), (c) Saline 0.5 ml.

Figure 6:
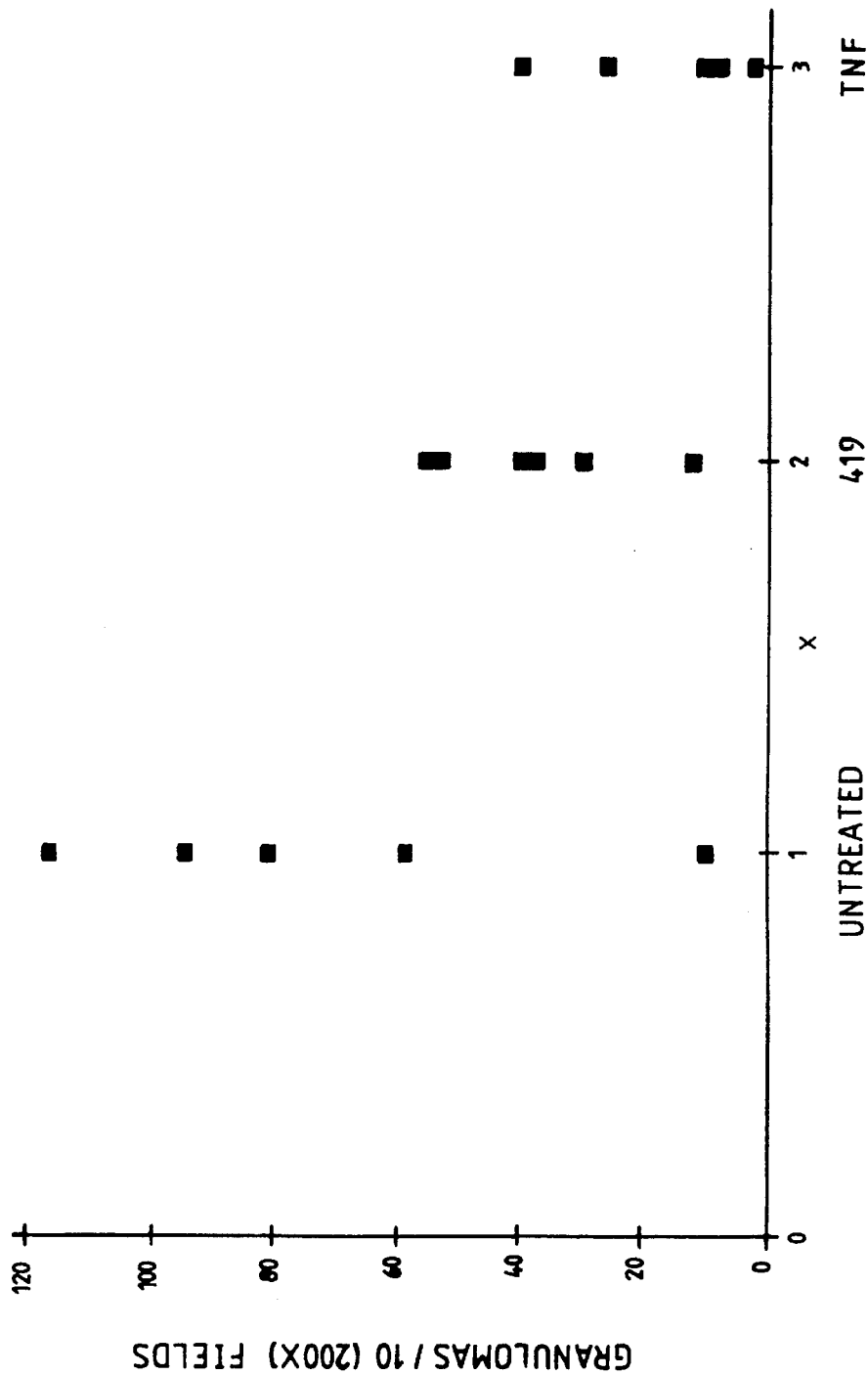
FIG. 6 shows the effect of peptide 419 [SEQ ID NO. 18] granuloma formation in mice infected with *Bacillus calmette gaurin;*

At day 11 the mice were sacrificed for enumeration of the number of granulomas in the liver. The results are shown in FIG. 6.

These results are strongly indicative that peptide 419 [SEQ ID NOS. 18] may have a therapeutic role in the treatment of granulomatous diseases.

Pseudomona Experiment

Chronic lung infection by *Pseudomonas aeruginosa* (Pa) is common in cystic fibrosis. Although the disease is dominated by a chronic excess of neutrophils, in vitro studies (Ferrante et al. submitted) suggest that these cells may not be receptive to activation by TNF for antibacterial activity. The present inventors reasoned that pre-sensitising neutrophils with TNF intravascularly, prior to their entry into the lung, may overcome this problem. Since TNF would not be useful as a therapeutic agent if used in this manner, because of its toxic side effects such as intravascular coagulation, the 11-amino acid peptide 419 which retains the neutrophil priming properties but lacks the toxicity of TNF was used. The ability of i.v.-injected 419 [SEQ ID NOS. 18] to protect against chronic lung injury induced by Pseudomonas was tested. Chronic lung infections were established in 120 14 week female Swiss mice by introducing the bacteria suspended in agar beads (<200 μm diameter) into the lung. Mice were anaesthetised and 30 μl of bead suspension introduced via a polyethylene cannula into the right bronchus through a small incision between the tracheal rings. After recover, animals (n=20) developed a chronic infection followed for at least 10–14 days. Control animals included: sham-operated (n=2); and those inoculated with sterile beads (n=6) or with beads containing fresh, heat-killed Pa (n=5). Eight of the 20 infected animals were treated with either the "419" [SEQ ID NOS. 18] peptide (n=4) (or with saline carrier, (n=4), receiving 100 μl of 0.5 mg peptide (or carrier) by tail-vein injection, each day for 3 days from day 12. After sacrifice, lungs were perfusion-fixed with formalin and sections (masked to treatment type) were assessed histologically for the extent of inflammation. In this continuing study, chronically-infected animals showed extensive inflammatory reactions in the bronchi and the parenchyma. Control groups revealed negligible inflammation. The animals treated with peptide 419 showed significantly less percentage peripheral consolidation (mean (0.25 (se 0.25)) than the carrier-treated animals (mean 5.25 (se 1.84) p<0.05 Mann-Whitney). These results suggest that the TNF-derived peptide "419" [SEQ ID NOS. 18] may be beneficial in the treatment of chronic pseudomonal lung infection. Further, these results suggest that peptide 419 [SEQ ID NOS. 18] may have a therapeutic role in the treatment of lung infection in patients suffering from cystic fibrosis or who are immunosuppressed.

Effect Of Peptide 419 on monocytes

Peptide 419 [SEQ ID NOS. 18] was assayed for its ability to prime monocytes for a respiratory burst. This assay was conducted essentially as described above for neutrophils except that the cells were cultured for 24 hours prior to assay. The results are set out in Table 7.

TABLE 7

| | Peak mV Chemiluminescence | | |
|---|---|---|---|
| | 1 | 2 | Mean ± S.D. |
| +HBSS | 1.72 | 1.46 | 1.59 ± 0.184 |
| +fMLP | 104 | 114.0 | 109.0 ± 7.071 |
| +419 [SEQ ID NO. 18] | 2.42 | 4.35 | 3.385 ± 1.365 |
| +419 + fMLP | 263.0 | 217.0 | 240.0 ± 32.527 |
| +TNF | 2.03 | 1.74 | 1.885 ± 0.206 |
| +TNF + fMLP | 104.0 | 163.0 | 133.5 ± 41.719 |

$10^6$ monocytes/tube/ml
50 U TNF 30 min pre-incubation at 37° C.
Peptide 419 100 μg/$10^6$ monocytes—30 mins preincubation at 37° C.

In Socher et al., 1987 (PNAS:84:8829–8833)a peptide having some similarity to the peptides of the present invention is disclosed. The disclosed peptide is a fragment of TNF from residues 65–79. This peptide was synthesized by the present applicant and is referred to herein as "peptide 462" [SEQ ID NOS. 19].

Peptide 462 [SEQ ID NOS. 19] was assayed for its ability to prime neutrophils for a respiratory burst in comparison with peptide 419 [SEQ ID NOS. 18] using the protocol set out above. The results obtained are set out in Table 8A.

TABLE 8A

| Treatment | Chemiluminescence mean + sem (mV) |
|---|---|
| HBSS | 4.1 ± 0.3 |
| 462 [SEQ ID NO. 19] (1 μg) | 3.1 ± 0.5 |
| 462 (10 μg) | 4.8 ± 0.7 |
| 462 (100 μg) | 4.8 ± 0.5 |
| 419 [SEQ ID NO. 18] (100 μg) | 18.6 ± 0.5 |

It is clear from these results that whilst peptide 462 [SEQ ID NOS. 19] may bear some superficial similarity to the peptides of the present invention it does not possess the biological activity of those peptides.

Induction of ICAM on human umbilical vein endothelial cells (HUVEC)

TNF is known to induce ICAM and it is thought that this activity contributes to its toxicity in vivo. Peptide 419 [SEQ ID NOS. 18] was tested for its ability to induce ICAM using the following procedure.

Confluent HUVEC, grown in M199 supplemented with foetal calf serum, endothelial growth factor and heparin were treated with either TNF (100 units) or peptide 419 [SEQ ID NOS. 18] (1 mg) for four hours at 37° C. The cells were then washed extensively with PBS containing $Ca^{++}$ and $Mg^{++}$ and fixed (100 ml 0.025% guteraldehyde, overnight, 4° C.) The cells were again washed, and 4° C. incubated with anti-ICAM antibody (84H10) for 1 hr at room temperature. The cells were washed and incubated for a further 1 hr at room temperature in the presence of rabbit anti-mouse Ig-HRP. Surface expression of Icam was then quantitated using the ABTS substrate by absorption at OD405 nm.

Figure 7:
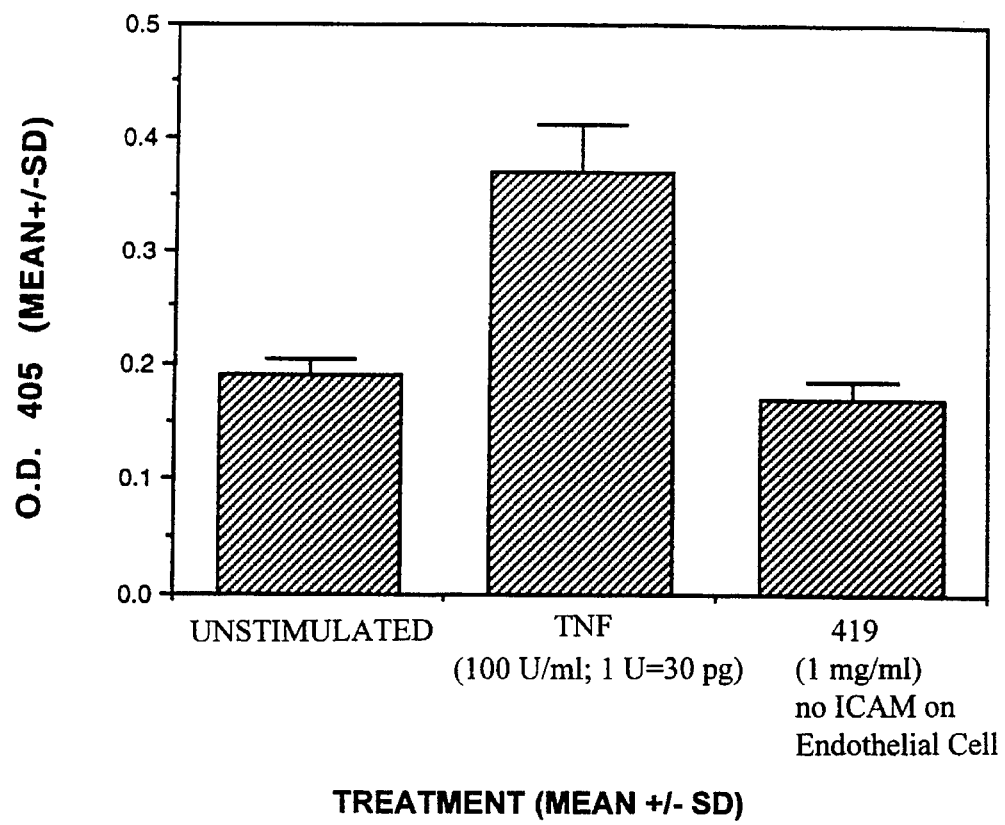
FIG. 7 shows that peptide does not induce the cell adhesion molecule ICAM or human umbilical vein endothelial cells.
Figure 8:
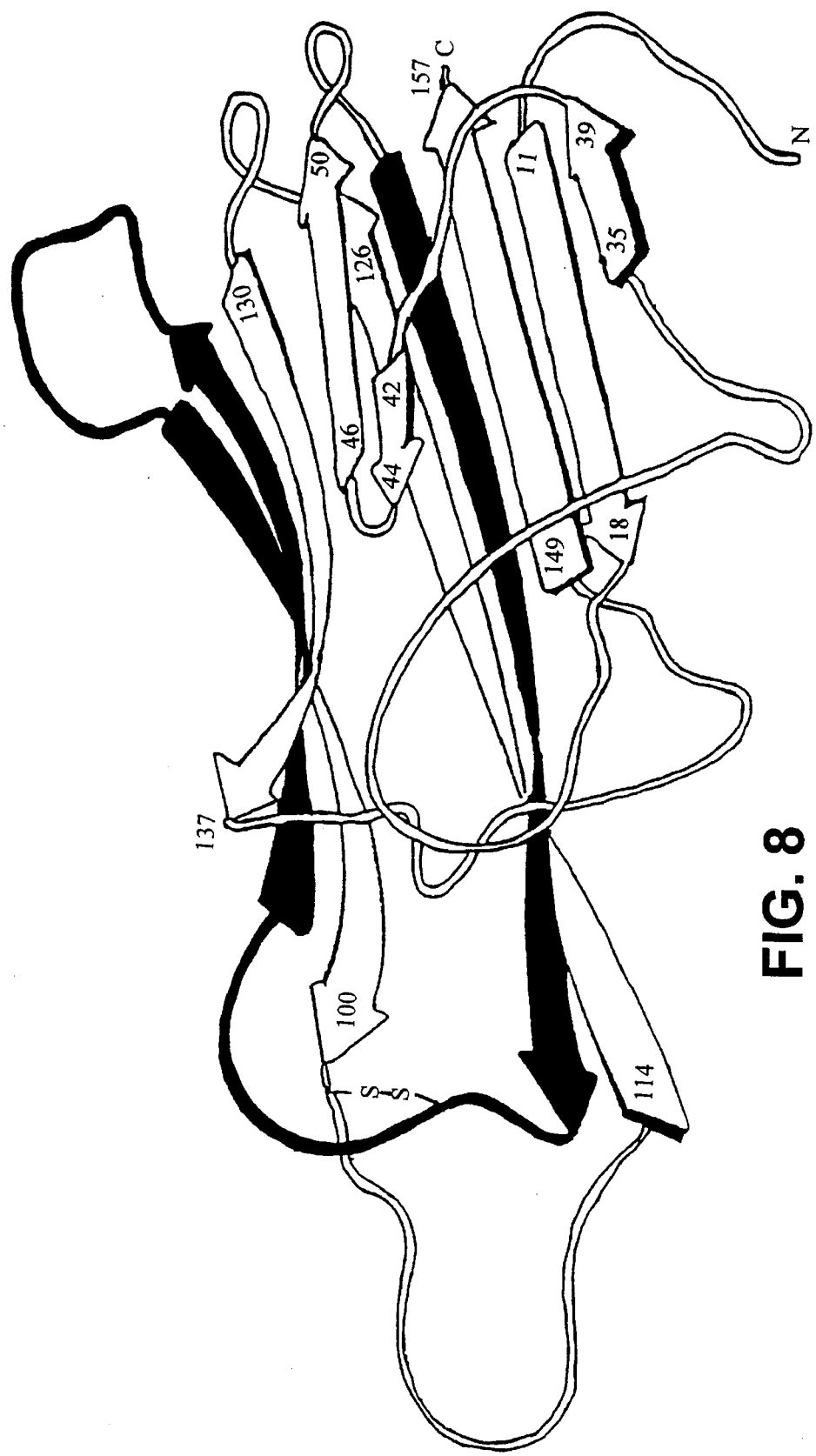
FIG. 8 is a representation of the TNFα monomer showing the position of the neutrophil stimulating peptides.

The results of the assay on peptide 419 [SEQ ID NOS. 18] are shown in FIG. 7. As can be seen peptide 419 [SEQ ID NOS. 18] does not induce the cell adhesion molecule ICAM on human umbilical vein endothelial cells. This clearly suggests that peptide 419 [SEQ ID NOS. 18] would be less toxic in vivo than TNF.

Effect of TNF peptides on neutrophil random migration

Migration of cells is an important property by which cells reach infection sites. Their accumulation at these sites is also dependent on the capacity of inflammatory mediators to inhibit their migration out of the sites. The present inventors have examined TNF and peptide 304, 308 and 309 [SEQ ID NOS. 6, 10, 11] for their effect on the migration of neutrophils.

In these experiments neutrophils were pre-treated with the peptide or TNF and then examined their ability to migrate out of wells in agarose as described by Ferrante et al, 1988, (Arch. Allergy Appl. Immunol. 86:82–91). The results are shown in Table 8. The results show that TNF was only partially migration inhibitory at 100 units/$10^6$ cells. Both peptides 308 [SEQ ID NOS. 10] and 309 [SEQ ID NO. 11] were potent migration inhibitors, however, peptide 304 [SEQ ID NO. 6] was found to be chemokinetic (it stimulated cell migration).

TABLE 8B

| | Inhibition of Migration μg/$10^6$ cells) | | |
|---|---|---|---|
| Treatment | 0 | 10 | 100 |
| TNF | ND | ND | 4% |
| 304* [SEQ ID NOS. 6,10,11] | −16% | −43% | −883% |
| 308 [SEQ ID NOS. 6,10,11] | 0 | 0 | 100% |
| 309 [SEQ ID NOS. 6,10,11] | 0 | 0 | 100% |

*Peptide 304 was found to stimulate (chemokinetic)

Chemotactic properties of TNF and peptides

The chemotactic properties of TNF and peptides 304, 308 and 309 [SEQ ID NOS. 6, 10, 11] were examined using the following method:

3 ml of molten 2% agarose was mixed with 3 ml of 2× concentrated medium 199 containing foetal calf serum (10%) and poured into Petri dishes. Sets of 3 wells of 2.5 mm diameter, each 3 mm apart, were cut in the agarose. 5 μl of neutrophils ($2\times10^5$ cells) were added to the inner well, with chemotactic agent or control medium added to the outer wells. Migration at various time intervals was then measured.

The results of these experiments are shown in Table 9.

TABLE 9

| | Migration distance (mm) at | | | |
|---|---|---|---|---|
| | 1.5 h | | 2.5 h | |
| Agent* | None | Agent | None | Agent |
| fMLP | 0.50 | 1.46 | 0.66 | 2.45 |
| TNF | 0.50 | 0.48 | 0.66 | 0.69 |
| 304 [SEQ ID NO. 6,10,11] | 0.48 | 0.47 | 0.68 | 0.72 |
| 308 [SEQ ID NO. 6,10,11] | 0.50 | 0.66 | 0.63 | 1.41 |
| 309 [SEQ ID NO. 6,10,11] | 0.50 | 0.53 | 0.63 | 0.68 |

*To the chemotactic well was added 5 ml of $1 \times 10^{-7}$ MfMLP, of either peptide 304; peptide 308 and peptide 309 or $10^3$ U/ml of TNFα

Effect of TNF Peptides on Neutrophil Degranulation

The conditions of measuring degranulation were as described by Ferrante A, 1989, (Infect and Immunity 57, 3110–3115). In these studies 100 μl of neutrophils ($10^7$/ml)

were incubated for 20 min at 37° C. after which 10 μl of cytochalasin B was added. After 10 min incubation the volume of cell suspension was made up to 1 ml with Hanks Balanced Salt Solution (HBSS). The cell-free supernatants were collected and analysed for enzyme levels after a further incubation at 37° C. Dβ-Glucuronidase activity was measured fluorimetrically by using 4-methylumbelliferyl-β-D-glucuronide as substrate. This involved incubating 50 μl of 2.5 mM substrate in 0.1M citric acid-sodium phosphate buffer, pH 4.5, at 37° C. for 3 h. The reaction was stopped by adding 1.5 ml of 0.2M glycine-sodium hydroxide buffer, pH 10.7 and the fluorescence of the liberated 4-methylumbelliferone was quantitated by using excitation and emission wavelengths of 336 and 446 nm, respectively. Vitamin $B_{12}$ binding protein was measured using $^{57}$Co-vitamin $B_{12}$. This assay is based on the principle that the binding protein binds to the $^{57}$Co-Vitamin $B_{12}$ and as a result the radioactive vitamin $B_{12}$ does not bind to charcoal. The resultant radioactivity in the supernatant can then be equated to the concentration of vitamin $B_{12}$-binding protein in the sample. The results of these experiments are set out in Table 10 A and B.

TABLE 10

Effect of TNF Peptides in Neutrophil Degranulation
Neutrophils were treated with 100 μg/10⁶ cells of 304, 305 or 308 [SEQ ID NOS, 6,7,10] ± fMLP (in the presence of CytoB).

A.

| Treatment | β-glucuronidase release (%) | | | |
|---|---|---|---|---|
| | Exp. 1 | Exp. 2 | Exp. 3 | Exp.4 |
| HBSS | 3.63 | 1.84 | 2.72 | 6.23 |
| HBSS + fMLP | 23.62 | 41.41 | 40.19 | 27.54 |
| 304 | 3.63 | 3.14 | 2.52 | 9.82 |
| 304 + fMLP | 26.95 | 36.43 | 35.34 | 36.65 |
| Control peptide | — | — | — | 13.41 |
| Control peptide + fMLP | — | — | — | 35.69 |
| 308 | 0.8 | 0.65 | 2.76 | 0.72 |
| 308 + fMLP | 17.57 | 28.86 | 17.86 | 18.20 |

B.

| Treatment | Vitamin $B_{12}$ Binding Protein | | | |
|---|---|---|---|---|
| | Exp. 1 | Exp. 2 | Exp. 3 | Exp.4 |
| HBSS | 9.21 | 9.27 | 9.67 | 4.80 |
| HBSS + fMLP | 28.85 | 27.91 | 45.31 | 27.33 |
| 304 | 11.40 | 10.82 | 13.06 | 8.42 |
| 304 + fMLP | 43.76 | 35.60 | 59.15 | 37.12 |
| Control peptide | — | — | — | 7.49 |
| Control peptide + fMLP | — | — | — | 38.62 |
| 308 | 2.00 | 2.08 | 5.70 | 2.25 |
| 308 + fMLP | 35.81 | 27.59 | 26.55 | 21.51 |

The effects of TNFα peptides on stimulation of neutrophil respiratory burst, degranulation, migration inhibition, chemokinesis and chemotaxis were investigated. As can be seen from the results set out above only peptides 304, 308 and 309 [SEQ ID NOS. 6, 10, 11] were found to prime human neutrophils for the respiratory burst associated with f-met-leu-phe treatment, i.e. in a manner analogous to that of TNFα. Together these peptides comprise the primary amino acids sequence region of amino acids 54 to 94 of human TNFα. Peptide 308 [SEQ ID NO. 10] is a particularly potent primer of neutrophils in this assay.

It is to be noted, however, that peptide 323 [SEQ ID NO. 12] which has a sequence which corresponds to amino acids 79 to 89 of human TNF was not found to be capable of priming neutrophils for the respiratory burst associated with f-met-leu-phe treatment. The reason for the lack of neutrophil stimulating activity of this peptide has not as yet been elucidated, however, one hypothesis for the lack of activity of this peptide may be that peptide 323 [SEQ ID NO. 12] does not include the amino acid residues which bind to the TNF receptor on the neutrophils.

Peptides 308 and 309 [SEQ ID NOS. 10,11] have also been found to be potent inhibitors of neutrophil migration whilst peptide 304 [SEQ ID NO. 6] has been found to be chemokinetic. Peptide 308 [SEQ ID NO. 10] has also been found to be strongly chemotactic.

The effects of TNF peptides 304 [SEQ ID NOS. 6,10] and 308 on degranulation of neutrophils (Table 10) showed that peptide 308 [SEQ ID NO. 10] decreased the release of the contents of both the specific and the azurophilic granules as measured by the release of Vitamin $B_{12}$ binding protein and β-glucuronidase release respectively. This effect of peptide 308 [SEQ ID NO. 10] was still apparent following stimulation with fMLP. In contrast, peptide 304 [SEQ ID NO. 6] had no effect on neutrophil degranulation in the absence of fMLP. In the presence of fMLP peptide 304 [SEQ ID NO. 6] enhanced release from specific granules but not azurophilic granules.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A peptide having the formula: Leu-Phe-Lys-Gly-Gln-Gly-Cys-Pro-Ser-Thr-His-Val-Leu-Leu-Thr-His-Thr-Ile-Ser-Arg-Ile (SEQ ID NO.:6).

2. A peptide having the formula: Gly-Leu-Tyr-Leu-Ile-Tyr-Ser-Gln-Val-Leu-Phe-Lys-Gly-Gln-Gly (SEQ ID NO.:10).

3. A peptide having the formula: His-Val-Leu-Leu-Thr-His-Thr-Ile-Ser-Arg-Ile-Ala-Val-Ser-Tyr-Gln-Thr-Lys-Val-Asn-Leu-Leu ( SEQ ID NO.: 11.).

4. A peptide having the formula: Pro-Ser-Thr-His-Val-Leu-Leu-Thr-His-Thr-Ile )SEQ ID NO.:15).

5. A peptide having the formula: Pro-Ser-Ala-His-Val-Leu-Leu-Thr-His-Thr-Ile (SEQ ID NO.:17).

6. A peptide having the formula: Pro-Ser-Thr-His-Val-Leu-Ile-Thr-His-Thr-Ile (SEQ ID NO.:18).

* * * * *